United States Patent [19]

Freitag et al.

[11] 4,001,183
[45] Jan. 4, 1977

[54] TETRAPHENOL CONTAINING POLYCARBONATES

[75] Inventors: Dieter Freitag; Ulrich Haberland; Heinrich Krimm, all of Krefeld-Bockum, Germany

[73] Assignee: Bayer Aktiengesellschaft, Leverkusen, Germany

[22] Filed: Mar. 13, 1975

[21] Appl. No.: 558,049

Related U.S. Application Data

[60] Continuation of Ser. No. 404,557, Oct. 9, 1973, which is a division of Ser. No. 285,699, Sept. 1, 1972, Pat. No. 3,799,953, which is a continuation-in-part of Ser. No. 178,443, Sept. 7, 1971, abandoned.

[30] Foreign Application Priority Data

Mar. 19, 1971 Germany .......................... 2113347

[52] U.S. Cl. .............................. 260/47 XA; 260/49
[51] Int. Cl.² ........................................ C08G 63/62

[58] Field of Search ......................... 260/47 XA, 49

[56] References Cited

UNITED STATES PATENTS 3,544,514  12/1970  Schnell et al. ............... 260/47 XA

FOREIGN PATENTS OR APPLICATIONS 715,142  8/1965  Canada .......................... 260/47 XA Primary Examiner—Wilbert J. Briggs, Sr.
Attorney, Agent, or Firm—Lawrence S. Pope; Gene Harsh

[57] ABSTRACT

The subject matter of the invention relates to 1,4-bis-(4',4''-dihydroxy-triphenyl-methyl)-benzene and to plastics, in particular to branched polycarbonates, on the basis of this tetra-hydroxy-compound.

9 Claims, 1 Drawing Figure

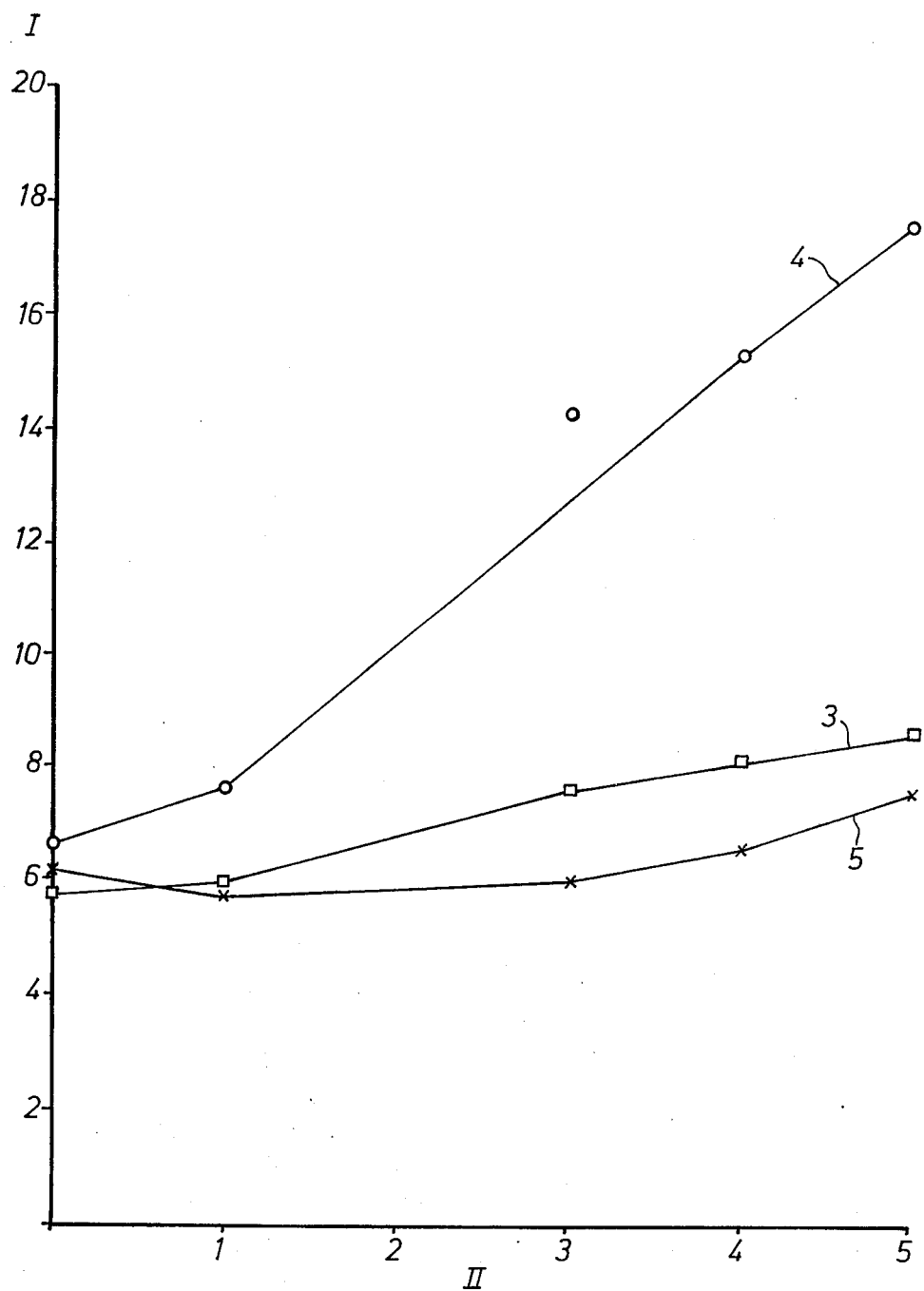

TETRAPHENOL CONTAINING POLYCARBONATES

This is a continuation application of Ser. No. 404,557, filed Oct. 9, 1973, which in turn is a division, of application Ser. No. 285,699 filed Sept. 1, 1972, now U.S. Pat. No. 3,799,953 which is a continuation-in-part application of application Ser. No. 178,443, filed Sept. 7, 1971 now abandoned.

The subject matter of the invention relates to 1,4-bis-(4',4''-dihydroxy-tri-phenyl-methyl)-benzene and plastics, in particular to branched polycarbonates, on the basis of this tetra-hydroxy-compound.

According to the German Offenlegungsschrift No. 1 570 533 respectively U.S. Pat. application No. 3,544,514 more than bivalent phenols, such as phloroglucine, 4,6-dimethyl-2,4,6-tri-(4-hydroxyphenyl)-heptene-2, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane and 2,2-bis-[4,4-(4,4'-dihydroxydiphenyl)-cyclohexyl]-propane are suitable for the preparation of branched polycarbonates whose melts have improved stability.

It has now been found that when using 1,4-bis-(4,4''-dihydroxy-tri-phenyl-methyl)-benzene, polycarbonates are obtained which not only possess the advantages mentioned in the German Offenlegungsschrift No. 1 570 533 but also improved non-Newtonian flow behaviour and increased thermostability. The use of 1,4-bis-(4',4''-dihydroxy-tri-phenyl-methyl)-benzenes also has the advantage that this tetraphenol is effective in lower concentrations. The incorporation of the new tetraphenol in polycarbonates is carried out according to the U.S. Pat. specification No. 3,544,514 respectively to the German Offenlegungsschrift No. 1 570 533.

There is no description of 1,4-bis-(4',4''-dihydroxy-triphenyl-methyl)-benzene in the past literature.

It is prepared according to the invention by condensation of 1,4-bis-(α,α-dichloro-benzyl)-benzene with phenol in accordance with the given formula scheme, the 1,4-bis-(α,α-dichloro-benzyl)-benzene being obtainable either by chlorination of 1,4-dibenzyl-benzene or by chlorination of 1,4-di-benzoyl-benzene according to processes known from the literature:

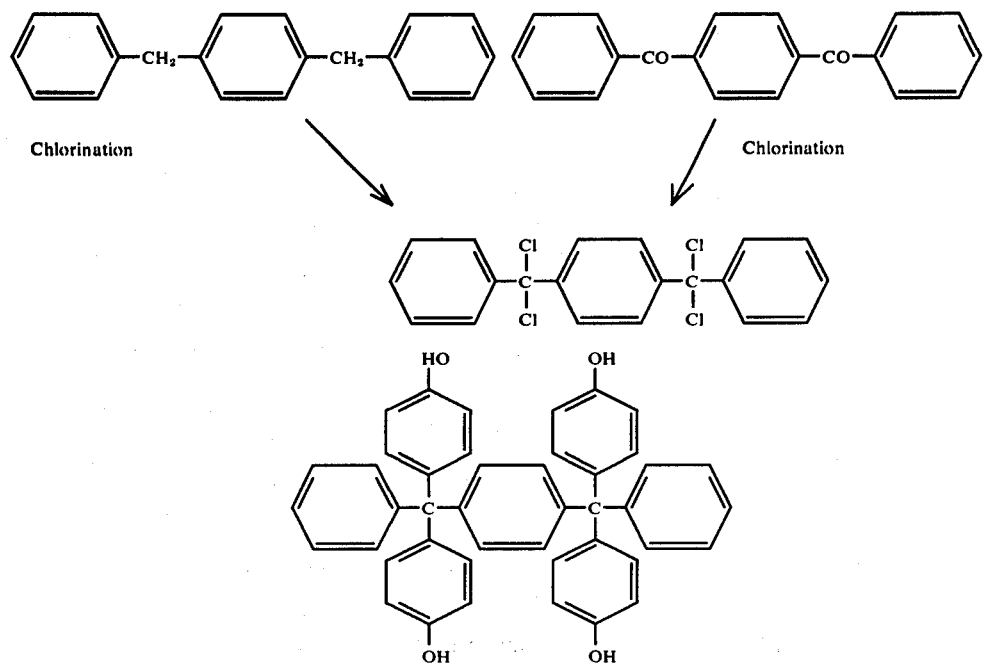

The new compound is colourless and crystalline. It melts at 314° – 316° C and dissolves in the conventional organic solvents such as dioxane, acetone, methanol, ethanol, glacial acetic acid, dimethyl formamide and dimethyl sulphoxide as well as in organic bases such as triethylamine, quinoline, pyridine, and inorganic bases such as dilute potassium hydroxide solution and sodium hydroxide solution. The alkaline solutions are colourless and not sensitive to air.

The structure of the 1,4-bis-(4',4''-dihydroxy-triphenyl-methyl)-benzene is ensured by elementary analysis, infrared and NMR spectrum. Elementary analysis $C_{44}H_{34}O_4$ (626.71).

| Calculated: | | | Found: | | |
|---|---|---|---|---|---|
| | C: | 84,32 % | | C: | 84,2 – 84,4 % |
| | H: | 5,47 % | | H: | 5,47 % |
| | O: | 10,21 % | | O: | 10,2 – 10,4 % |
| | OH: | 10,87 % | | OH: | 11,0 – 11,2 % |

The reaction of the 1,4'-bis-(α, α-dichloro-benzyl-benzene to form 1,4-bis-(4',4''-dihydroxy-tri-phenyl-methylbenzene is carried out at temperature betweens 10° – 150° C, preferably between 50° – 140° C, by bringing the reactants together possibly in the presence of diluents. The reaction course can be controlled by the amount of hydrogen chloride which has been split off.

Metal halides, such as aluminum chloride, boron trifluoride, zinc chloride or tin tetrachloride as well as halides of phosphor, such as phosphorus trichloride, phosphorus pentachloride as well as phosphoroxy chloride can be added. Suitable diluents are for example glacial acetic acid, dioxane, aromatic hydrocarbons such as benzene, toluene, xylene as well as hexane or petroleum ether.

The multivalent phenol formed during the reaction precipitates in the presence of the above-mentioned diluents from the reaction solution. To purify the compound it is removed from the solid product by suction filtration and, if necessary, the residue is recrystallised from o-dichlorobenzene.

The yield of pure 1,4-bis-(4',4''-dihydroxy-triphenylmethyl)-benzene is over 80 % of the theory based on the used 1,4-bis-(α;α-dichloro-benzyl)-benzene.

This new tetraphenol can be employed for the preparation of branched polycarbonates which may be produced from any suitable dihydroxy compounds.

Therefore, another subject of the invention is a high molecular weight, branched polycarbonate substantially free of crosslinking which comprises a polycarbonate polymer containing residues of an organic dihydroxy compound, about 0.01 to about 1 mol percent of residues of 1,4-bis-(4',4''-dihydroxy-triphenylmethyl)-benzene and about 0.1 to about 8 mol percent of monohydric phenol, the mol percentages being based on the mols of the organic dihydroxy compound, said branched polycarbonate having a relative viscosity of from 1.2 to about 1.55 measured on a solution of 0.5 gram in 100 ml of methylene chloride at 20° C, an average molecular weight of between about 30,000 and about 100.000 measured by light diffusion and a melt viscosity of between 20.000 and about 300.000 poises at 280° C.

High molecular weight thermoplastic polycarbonates may be produced from any suitable dihydroxy compounds including aliphatic, cycloaliphatic and aromatic dihydroxy compounds. Some such suitable aromatic dihydroxy compounds include, for example, the dimonohydroxy arylene alkanes and the dimonohydroxy arylene sulphones such as, for example, 4,4'-dihydroxydiphenylene sulphone,
2,2-dihydroxydiphenylene sulphone,
3,3'-dihydroxydiphenylene sulphone,
4,4'-dihydroxy-2,2'-dimethyldiphenylene sulphone,
4,4'-dihydroxy-3,3'-dimethyldiphenylene sulphone,
2,2'-dihydroxy-4,4'-dimethyldiphenylene sulphone,
4,4'-dihydroxy-2,2'-diethyldiphenylene sulphone,
4,4'-dihydroxy-3,3'-diethyldiphenylene sulphone,
4,4'-dihydroxy-2,2'-di-tert.-butyl-diphenylene sulphone,
4,4'-dihydroxy-3,3'-di-tert.-butyl-diphenylene sulphone, and
2,2'-dihydroxy-1,1'-dinaphthylene sulphone,
4,4'-dihydroxy-diphenylene-methane,
1,1-(4,4'-dihydroxy-diphenylene)-ethane,
1,1-(4,4'-dihydroxy-diphenylene)-propane,
1,1-(4,4'-dihydroxy-diphenylene)-butane,
1,1-(4,4'-dihydroxy-diphenylene)-2-methyl-propane,
1,1-(4,4'-dihydroxy-diphenylene)-heptane,
1,1-(4,4'-dihydroxy-diphenylene)-1-phenyl-methane,
(4,4'-dihydroxy-diphenylene)-(4-methyl-phenylene)-methane,
(4,4'-dihydroxy-diphenylene)-(4-ethyl-phenylene)-methane,
(4,4'-dihydroxy-diphenylene)-(4-isopropyl-phenylene)-methane,
(4,4'-dihydroxy-diphenylene)-(4-butyl-phenylene)-methane,
(4,4'-dihydroxy-diphenylene)-benzyl-methane,
(4,4'-dihydroxy-diphenylene)-alpha-furyl-methane,
2,2-(4,4'-dihydroxy-diphenylene)-propane,
2,2-(4,4'-dihydroxy-diphenylene)-butane,
2,2-(4,4'-dihydroxy-diphenylene)-pentane,
2,2-(4,4'-dihydroxy-diphenylene)-4-methyl-pentane,
2,2-(4,4'-dihydroxy-diphenylene)-heptane,
2,2-(4,4'-dihydroxy-diphenylene)-octane,
2,2-(4,4'-dihydroxy-diphenylene)-nonane,
1,1-(4,4'-dihydroxy-diphenylene)-1-phenyl-ethane,
(4,4'-dihydroxy-diphenylene)-1-(alpha-furyl)-ethane,
3,3-(4,4'-dihydroxy-diphenylene)-pentane,
4,4'-(4,4'-dihydroxy-diphenylene)-heptane,
1,1-(4,4'-dihydroxy-diphenylene)-cyclopentane,
1,1-(4,4'-dihydroxy-diphenylene)-cyclohexane,
2,2-(4,4'-dihydroxy-diphenylene)-decahydronaphthalene,
2,2-(4,4'-dihydroxy-3,3'-dicyclohexyl-diphenylene)-propane,
2,2'-(4,4'-dihydroxy-3-methyl-diphenylene)-propane,
2,2-(4,4'-dihydroxy-3-isopropyl-diphenylene)-butane,
1,1-(4,4'-dihydroxy-3,3'-dimethyl-diphenylene)-cyclohexane,
2,2-(4,4'-dihydroxy-3,3'-dibutyl-diphenylene)-propane,
2,2-(4,4'-dihydroxy-3,3'-diphenyl-diphenylene)-propane,
2,2-(4,4'-dihydroxy-2,2'-dimethyl-diphenylene)-propane,
1,1-(4,4'-dihydroxy-3,3'-dimethyl-6,6'-ditert.-butyl-diphenylene)-ethane,
1,1-(4,4'-dihydroxy-3,3'-dimethyl-6,6'-ditert.-butyl-diphenylene)-propane,
1,1-(4,4'-dihydroxy-3,3'-dimethyl-6,6'-ditert.-butyl-diphenylene)-butane,
1,1-(4,4'-dihydroxy-3,3'-dimethyl-6,6'-ditert.-butyl-diphenylene)-isobutane,
1,1-(4,4'-dihydroxy-3,3'-dimethyl-6,6'-ditert.-butyl-diphenylene)-heptane,
1,1-(4,4'-dihydroxy-3,3'-dimethyl-6,6'-ditert.-butyl-diphenylene)-1-phenyl-methane,
1,1-(4,4'-dihydroxy-3,3'-dimethyl-6,6'-ditert.-butyl-diphenylene)-2-methyl-2-pentane,
1,1-(4,4'-dihydroxy-3,3'-methyl-6,6'-ditert.-butyldiphenylene)-2-ethyl-2-hexane,
1,1-(4,4'-dihydroxy-3,3'-dimethyl-6,6'-ditert.-butyl-diphenylene)-butane, the corresponding bis-hydroxyphenyl ethers, sulphides sulphoxides and the like.

Among the great number of suitable di-monohydroxy arylene alkanes which may be used are the 4,4'-dihydroxy-diphenylene alkanes and it is preferred that of this class of compounds
2,2-(4,4'-dihydroxy-diphenylene)-propane,
bis-(4-hydroxy-3,5-dichlorophenyl)-propane-2,2,
bis-(4-hydroxy-3,5-dibromo-phenyl)-propane-2,2,
bis-(4-hydroxy-3,5-dimethyl-phenyl)-propane-2,2
and
1,1-(4,4'-dihydroxy-diphenylene)-cyclohexane be used.

Any suitable aliphatic dihydroxy compounds may be used including, for example, ethylene glycol, diethylene glycol, triethylene glycol, polyethylene glycol, thiodiglycol, ethylene dithioglycol, the di- and poly-glycols produced from propylene oxide-1,2, o, m or p-xylyene glycol, propanediaol-1,3, butanediol-1,3, butanediol-1,4, 2-methyl-propanediol-1,3, pentanediol-1,5, 2- ethylpropanediol-1,3, hexanediol-1,6, octanediol-1,8, 1-ethylhexanediol-1,3, decanediol-1,10 and the like.

Any other suitable aromatic dihydroxy compounds may also be used. Some such suitable compounds include hydroquinone, resorcinol, pyrocatechol, 4,4'-dihydroxydiphenyl, 2,2'-dihydroxydiphenyl, 1,4-dihydroxynaphthalene, 1,6-dihydroxynaphthalene, 2,6-dihydroxynaphthalene, 1,2-dihydroxynaphthalene, 1,5-dihydroxynaphthalene, dihydroxy anthracene, 2,2'-dihydroxynaphthalene, 1,1'-and o, m and p-hydroxybenzyl alcohol and the like.

Any suitable cycloaliphatic dihydroxy compounds may be used including cyclohexanediol-1,4, cyclohexanediol-1,2, 2,2-(4,4'-dihydroxy-dicyclohexylene)-propane, 2,6-dihydroxy decahydronaphthalene, the corresponding bis-alkoxylated aromatic dihydroxy compounds thereof and the like.

Any suitable monohydric phenols may be used to prepare the polycarbonate of this invention. Some such suitable compounds include, for example, phenol, lower alkyl phenols such as, for example, 4-methylphenol, 3-ethylphenol, 5-propylphenol, 4-isopropylphenol, 5-butylphenol, 3-isobutylphenol, 4-tertiary butylphenol, 4-pentylphenol and the like; aryl phenols such as, for example, 4-phenyl phenol, 5-phenyl phenol and the like; cycloaliphatic phenols such as, for example, 4-cyclohexyl phenol, 3-cyclopentyl phenol and the like; monophenol alkanes such as, for example, 2,2-(4-hydroxyphenyl)-4-methoxyphenyl)-propane, 3-hydroxyphenyl ethane.

The formation of the high molecular weight polycarbonates by the reaction of di-(monohydroxyaryl)-alkanes with derivatives of carbonic acid may be carried out by the conventional technique known in the art. For example phosgene can be introduced into a solution of di-(monohydroxyaryl)-alkanes in organic bases such as dimethylaniline, diethylaniline, trimethylamine and pyridine, or into solutions or d-(monohydroxyaryl)-alkanes in indifferent organic solvents such as benzene, ligroin, cyclohexane, methylcyclohexane, benzene, toluene, xylene, chloroform, methylenechloride, carbon tetrachloride, trichloroethylene, trichloroethane, methyl acetate and ethyl acetate with the addition of an acid binding agent.

A process particularly suitable for producing polycarbonates consists of introducing phosgene into an aqueous solution of alkali metal salts such as lithium, sodium, potassium and calcium salts of the di-(monohydroxyaryl)-alkanes, preferably in the presence of an excess of a base such as lithium, sodium, potassium and calcium hydroxide or carbonate. The polycarbonate precipitates out from the aqueous solution.

The conversion in the aqueous solution is promoted by the addition of indifferent solvents of the kind mentioned above which are capable of dissolving phosgene and eventually the produced polycarbonate.

It is also possible to react the di-(monohydroxyaryl)alkanes with equal molecular amounts of bis-chlorocarbonic acid esters of di-(monohydroxyaryl)-alkanes under corresponding conditions.

Also, the di-(monohydroxyaryl)-alkanes can be re-esterified with carbonic acid diesters, e.g. dimethyl, diethyl, dipropyl, dibutyl, diamyl, dioctyl, dicyclohexyl, diphenyl and di-, o-, p-tolyl carbonate at elevated temperatures from about 50° C to about 320° C and especially from about 120° C to about 280° C.

When using phosgene or bis-chlorocarbonic acid esters as derivatives of the carbonic acid in producing polycarbonates, catalysts may also be advantageous. Such catalysts are, for example, tertiary or quaternary organic bases or salts thereof such as trimethylamine, triethylamine, dimethylaniline, diethylaniline, dimethylcyclohexylamine and pyridine, for instance, the corresponding hydrochlorides and tetramethylammonium hydroxide, triethyloctadecyl ammonium chloride, trimethylbenzylammonium fluoride, triethylbenzylammonium chloride, dimethyldodecyl ammonium chloride, dimethylbenzylphenyl ammonium chloride, trimethylcyclohexyl ammonium bromide and N-methylpyrodonium chloride in amounts of from about 0.002 to about 0.5 % by weight. These compounds may be added to the reaction mixture before or during the reaction.

The reaction of dihydroxy compounds such as di-(monohydroxyaryl)-alkanes with phosgene or the chlorocarbonic acid esters of di-(monohydroxy)-alkanes in the presence of the polyhydric phenols and monohydric phenols may be carried out at room temperature or at lower or elevated temperatures, that is to say, at temperatures of from the freezing point up to about the boiling point of the mixture and preferably from about 0° C to about 100° C. The reaction conditions should be such that about one mol of phosgene reacts with about one mol of the dihydroxy compounds.

By addition of from about 0.01 − 1 and preferably from about 0.05 − 0.5 mol percent of 1,4-bis-(4',4''-dihydroxy-triphenyl-methyl)-benzene and from about 0.1 to about 8, and preferably from 1 − 6 mol percent of monohydric phenols based on the mols of dihydroxy compound, it is possible to produce thermoplastic polycarbonates which contain a certain degree of branching but which are substantially free of crosslinking. In addition, these polycarbonates have a relative viscosity ranging from about 1.20 to about 1.55, an average molecular weight of between 30.000 and about 100.000 and a melt viscosity of between 20.000 and about 300.000 poises measured at 280° C.

In the formation of polycarbonates from either the solution polymerization reaction of the interfacial polycondensation reaction it is necessary to add both the 1,4-bis-(4',4''-dihydroxy-triphenyl-methyl)-benzene and the monohydric phenols to the hydroxy compounds which are reacted with phosgene or bis-chlorocarbonic acid esters in order to obtain the desired polycarbonate product having the desired properties of this invention. However, in the transesterification reaction, i.e. in the case of the reaction of the bis-phenols with carbonic acid aryl esters in the melt, it is only necessary to add the 1,4-bis-(4',4''-dihydroxy-triphenyl-methyl)-benzene in the above stated amounts and thus omit the addition of the monohydric phenols providing care is taken to prevent the monohydric phenols providing care is taken to prevent the monohydric phenol which is liberated by the reaction from the diaryl carbonate from being completely removed from the reaction mixture. As long as the monohydric phenol is present in the amount specific above, it will automatically participate in the synthesis of the polycarbonates.

Furthermore, in some of these cases, it is preferred to add surface active agents such as alkali metal salts of higher fatty acids of sulphonic acids or of higher aliphatic or aromatic hydrocarbons and polyoxyethylated alcohols and phenols. Greater amounts of the quaternary ammonium bases mentioned above act as surface active agents.

Additives of all kinds can be added before, during or after the production of the polycarbonates. For example, additives such as dyestuffs, pigments, stabilizing agents against the effect of moisture, heat, ultra-violet radiation, lubricants, fillers such as glass powder, quartz products, graphite, molybdenum, disulphide, metal powders, powders of high melting synthetic resins, e.g. polytetrachloroethylene powder, natural fibers such as cotton and asbestos, as well as glass fibers of the most varied types, metal fibers as well as fibers which are stable during residence in the melt of the polycarbonate and do not markedly damage the polycarbonate may be added to the polycarbonate composition.

The polycarbonates produced according to the present invention are elastic thermoplastic materials which are soluble in a variety of organic solvents which can be worked up from solutions into shaped articles such as films, fibers or the like or into lacquer coatings. A polycarbonate which is prepared by this invention can be easily fabricated into useful articles, films, fibers, sheets, tubes, rods and the like from a melt or solution thereof by conventional shaping techniques such as melding, casting or extruding. Also, these polycarbonates can be used to make laminates such as safety glass, or to prepare protective or decorative coatings.

In order that those skilled in the art may better understand how the present invention may be practiced, the following examples are given by way of illustration and not by way of limitation. The relative viscosities being measured on solutions of 0.5 g of the product in 100 ml methylene chloride at 25° C.

EXAMPLE 1

162 g of 1,4-dibenzoyl benzene and 708.7 g of phosphorus pentachloride are heated for 5 hours to about 135° C; thereafter all volatile components are removed in the waterpump vacuum at a bath temperature of 160° C. 221 g residue are obtained which correspond to a 98.3 % crude yield of 1,4-bis-($\alpha,\alpha$-dichloro-benzyl)-benzene. The 1,4-bis-($\alpha,\alpha$-dichloro-benzyl)benzene thus obtained is then added dropwise at 72° C within 90 minutes to a solution of 525 g of phenol and 300 ml of dioxane; thereafter the reaction mixture is heated up to 124° – 137° C and kept at this temperature for about 4 hours. After cooling the crystal paste is filtered off with suction, the residue is washed with a dioxane-ligroin (1:2) solution and dried. 1,4-bis-(4',4''-dihydroxy-triphenyl-methyl)-benzene yield: 292 g (83 % of the theory based on the crude 1,4-bis-($\alpha,\alpha$-dichlorobenzyl)-benzene). If necessary, the recrystallisation can be carried out from o-dichlorobenzene.

EXAMPLE 2

Preparation of a polycarbonate branched with the tetraphenol

Over a period of 2 hours at 24° – 26° C 1825 g of phosgene (15.8 mol) are introduced whilst stirring into a mixture of 3420 g of bis-2-(4-hydroxyphenyl)-propane (15 mol), 14.1 g of tetraphenol (0.0224 mol = 0.15 % mol), 67.5 g of p-tert.-butyl phenol (0.45 mol = 3 % mol), 4300 g of 45 % of sodium hydroxide solution (48 mol), 17.500 g of distilled water and 33.000 g of methylene chloride. Afterwards 6 g of triethylamine are added to this mixture. After stirring for a further hour the organic phase is separated off, washed several times with 2 % sodium hydroxide solution, 2 % phosphoric acid and distilled water and finally worked up by the addition of chlorobenzene and the distilling off of the methylene chloride. The chlorobenzene solution gels upon cooling and is further worked up in a granulator to form a mixture of powder and grains. The resulting product is dried for 48 hours in the waterpump vacuum at a temperature of 120° C.

The relative viscosity of the product thus obtained is 1.340. The mean weight of the molecular weight which is measured by light diffusion amounts to 48.700.

EXAMPLE 3

In a suitable reactor there are reacted hourly 60 kg of a solution of
- 131 kg 2,2-bis-(4-hydroxyphenyl)-propane (574 mol)
- 640 kg water
- 160 kg of a 45 % sodium hydroxide solution
- 50 g sodium boron hydride
- 2010 g tert.-butylphenol (13.4 mol, 2.3 mol % relative to bisphenol)
- 396 g 1,4-bis-(4',4''-dihydroxy-triphenyl-methyl)-benzene (0.11 mol % relative to bisphenol)

with 4.75 kg phosgene in 90 kg methylene chloride/chlorobenzene (1:1) and 3.05 kg sodium hydroxide solution.

40 g triethylamine and 0.7 kg of a 45 % sodium hydroxide solution are added hourly to the resulting mixture and worked up after an average residence time of 35 minutes in a stirrer cascade. The organic phase is separated off and washed with sodium hydroxide solution, 2 % phosphoric acid and several times with pure water. After evaporation of the solution and extrusion of the melt, a granulate of relative viscosity 1.341 is obtained (measured in 0.5 % by weight solution in $CH_2Cl_2$, at 20° C). The molecular weight which is measured by light diffusion amounts to 443.100.

EXAMPLE 4

A branched polycarbonate which is produced according to Example 3 including 0.22 mol % of 2,6-bis-(2'-hydroxy-5'-methylphenylmethylene)-4-methyl-phenol instead of 396 g 1,4-bis-(4',4''-dihydroxy-triphenylmethyl)-benzene shows a relative viscosity of 1.340 and the molecular weight which is measured by light diffusion amounts to 38.800.

EXAMPLE 5

An unbranched polycarbonate which is produced according to Example 3 without 0.11 mol % 1,4-bis-(4',4''-dihydroxytriphenylmethyl)-benzene and including 2.100 g (2.4 mol % relative to bisphenol) of tert.-butylphenol instead of 2.010 g tert.-butylphenol, has a relative viscosity of 1.337 and the molecular weight which is measured by light diffusion amounts to 32.800.

In the diagram the thermostability of the polycarbonates produced in Examples 3 – 5 is compared.

The abscissa (II) gives the number of extrusions, the ordinate (I) gives the Yellowness Index (Y-I), determined according to ASTM-D 1925–63 T.

The change of colour is measured in relation to the number of extrusions in a S 30/20 D extruder at 300° C.

It can be seen from the diagram that the branched polycarbonate of the invention (line 3) has practically the same thermostability as unbranched polycarbonates (line 5); the colour shade is only one shade darker after 5 extrusion stages, whereas the branched polycarbonate produced with 2,6-bis-(2-hydroxy-5'-methylphenylmethylene)-4-methylphenol (line 4) for the purpose of comparison is dyed deep brown-yellow.

EXAMPLE 6

In a suitable reactor there are reacted hourly in a continuous process 57 kg of a solution of

| | |
|---|---|
| 130 kg | 2,2-bis-(4-hydroxyphenyl)-propane |
| 631 kg | water |
| 103 kg | of a 45% sodium hydroxide solution |
| 50 g | sodium boron hydride |
| 3000 g | tert.-butylphenol |
| 358 g | 1,4-bis-(4',4''-dihydroxy-triphenyl-methyl)-benzene |

(0.1 mol % relative to the sum of bisphenol) with 4.75 kg phosgene in 90 kg methylene chloride/chlorobenzene 1 : 1 and 1.9 kg sodium hydroxide solution whilst thoroughly stirring. A solution consisting of 60 g triethylamine, 12 kg 2,2-bis-(4-hydroxy-3,5-dibromo-phenyl)-propane, 1.8 kg of a 45% sodium hydroxide solution and 50 kg water are added hourly to the resulting precondensate and after an average residence time of 30 minutes in a stirrer cascade worked up in the manner described in Example 3.

| | |
|---|---|
| Relative viscosity: | 1.29 |
| Molecular weight measured by light diffusion: | 34600 |

EXAMPLE 7

1145 g phosgene are introduced at 20° C over 100 minutes into a mixture of

| | |
|---|---|
| 660 g | 2,2-bis-(4-hydroxyphenyl)-propane |
| 2475 g | 2,2-bis-(4-hydroxy-3,5-dichlorophenyl)-propane |
| 12 g | 1,4-bis-(4',4''-dihydroxy-triphenyl-methyl)-benzene |
| | (0.2 mol% relative to the sum of bisphenol) |
| 88 g | p-tert.-butylphenol |
| 4.8 g | triethylamine |
| 26.4 kg | water |
| 28.2 kg | methylene chloride |
| 1720 g | of a 45% sodium hydroxide solution |

By dropwise introduction of a further 505 g of a 45 % sodium hydroxide solution the pH value is kept at 11 – 11.5 during the reaction with phosgene. Thereafter, 24 g triethylamine and 355 g sodium hydroxide solution are added and stirring continued for 1 ½ hours. Working up is carried out as described in Example 2.

| | |
|---|---|
| Relative viscosity: | 1.270 |
| Molecular weight measured by light diffusion: | 53000 |

EXAMPLE 8

In a stainless steel 25 l capacity autoclave equipped with a stirrer 7.000 g of 2,2-(4',4''-dihydroxy-diphenyl)-propane, 6.700 g of diphenylcarbonate, 0.01 g of a disodium salt of bisphenol and 19.2 g (0.1 mol % relative to bisphenol) of 1,4-bis-(4',4''-dihydroxy-triphenylmethyl)-benzene are melted under nitrogen atmosphere. Subsequently about 5.100 g of phenol are distilled off with agitation at a pressure of about 100 mmHg while slowly increasing the melt temperature from 180° to 240° C. During 1 hour the pressure is then gradually reduced to about 0.8 mmHg and the temperature increased to 300° C.

The polycondensation is continued to an end over a period of 2 hours.

The melt is spun off from the autoclave and granulated in the usual manner.

The polymere has a relative viscosity of 1.298.

We claim:

1. A high molecular weight, branched polycarbonate substantially free of crosslinking which comprises a polycarbonate polymer containing residues of an aromatic dihydroxy compound, about 0.01 to about 1 mol percent of residues of 1,4-bis(4',4''-dihydroxy-triphenylmethyl)-benzene and about 0.1 to 8 mol percent of monohydric phenol, the mol percentages being based on the mols of the aromatic dihydroxy compound, said branched polycarbonate having a relative viscosity of from 1.2 to about 1.55 measured on a solution of 0.5 gram in 100 ml of methylene chloride at 20° C, an average molecular weight of between about 30,000 and about 100,000, measured by light diffusion and a melt viscosity of between 20,000 and about 300,000 poises at 280° C.

2. The high molecular weight, branched polycarbonate of claim 1 wherein the aromatic dihydroxy compound is selected from the group consisting of dimonohydroxy arylene alkanes and dimonohydroxy arylene sulphones.

3. The high molecular weight, branched polycarbonate of claim 2 wherein the dimonohydroxy arylene alkanes are 4,4'-dihydroxy-diphenylene alkanes.

4. The high molecular weight, branched polycarbonate of claim 3 wherein the 4,4'-dihydroxy-diphenylene alkanes are selected from the group consisting of:
2,2-(4,4'-dihydroxy-diphenylene)-propane;
bis-(4-hydroxy-3,5-dichlorophenyl)-propane-2,2;
bis-(4-hydroxy-3,5-dibromo-phenyl)-propane-2,2;
bis-(4-hydroxy-3,5-dimethyl-phenyl)-propane-2,2
and
1,1-(4,4'-dihydroxy-diphenylene)-cyclohexane.

5. The high molecular weight, branched polycarbonate of claim 1 wherein the monohydric phenol is selected from the group consisting of phenol, lower alkyl phenols, aryl phenols, cycloaliphatic phenols and monophenol alkanes.

6. The process of making a high molecular weight, branched polycarbonate substantially free of crosslinking by adding about 0.01 to about 1 mol percent of 1,4-bis-(4',4''-dihydroxy-triphenylmethyl)-benzene and about 0.1 to about 8 mol percent of monohydric phenol to a solution or dispersion of organic dihydroxy compounds, the mol percentages being based on the mols of the organic dihydroxy compounds and reacting this mixture with phosgene or chlorocarbonic acid esters of the dihydroxy compounds to produce branched polycarbonate having a relative viscosity of from 1.2 to about 1.55 measured on a solution of 0.5 gram in 100 ml of methylene chloride at 20° C, an average molecular weight of between about 30,000 and about 100,000 measured by light diffusion and a melt viscosity of between 20,000 and about 300,000 poises at 280° C.

7. The product of the process of claim 6.

8. In a process for the production of aromatic polycarbonates by the reaction of di-(monohydroxyaryl)- alkanes with phosgene or the chlorocarbonic acid esters of di-monohydroxyaryl)-alkanes in a two-phase mixture, the improvement wherein about 0.05 to 0.5 mol percent of 1,4-bis-(4',4''-dihydroxytriphenylmethyl)-benzene and 0.1 to 8 mol percent of monohydric phenols, both based on the mols of said di-(monohydroxyaryl)-alkanes, are added to said mixture whereby a branched polycarbonate having a relative viscosity of from 1.2 to about 1.55 measured on a solution of 0.5 grams in 100 ml of methylene chloride at 20° C, an average molecular weight of between about 30,000 and about 100,000 measured by light diffusion and a melt viscosity of between 20,000 and 300,000 poises at 280° C, is formed.

9. The product of the process of claim 8.

* * * * *